(12) United States Patent
Olsson

(10) Patent No.: US 10,386,347 B2
(45) Date of Patent: Aug. 20, 2019

(54) PRINTED GAS SENSOR AND DIGITAL EXPIRY DATE THEREOF

(71) Applicant: INNOSCENTIA AB, Malmö (SE)

(72) Inventor: Martin Andreas Olsson, Lund (SE)

(73) Assignee: INNOSCENTIA AB, Malm (SE)

( * ) Notice: Subject to any disclaimer, the term of this patent is extended or adjusted under 35 U.S.C. 154(b) by 174 days.

(21) Appl. No.: 15/119,186

(22) PCT Filed: Feb. 24, 2015

(86) PCT No.: PCT/SE2015/000010
§ 371 (c)(1),
(2) Date: Aug. 16, 2016

(87) PCT Pub. No.: WO2015/126306
PCT Pub. Date: Aug. 27, 2015

(65) Prior Publication Data
US 2017/0052160 A1    Feb. 23, 2017

(30) Foreign Application Priority Data

Feb. 24, 2014  (SE) ..................... 1430023

(51) Int. Cl.
*G01N 31/22* (2006.01)
*G06Q 50/28* (2012.01)
(Continued)

(52) U.S. Cl.
CPC ......... *G01N 31/229* (2013.01); *G01N 27/127* (2013.01); *G01N 31/223* (2013.01);
(Continued)

(58) Field of Classification Search
CPC .. G01N 31/229; G01N 31/223; G01N 27/127; G01N 33/02; G01N 33/0036;
(Continued)

(56) References Cited

U.S. PATENT DOCUMENTS

| | | |
|---|---|---|
| 6,815,211 B1 | 11/2004 | Blazewicz et al. |
| 2005/0248455 A1 | 11/2005 | Pope et al. |
| 2006/0121613 A1 | 6/2006 | Havens |

FOREIGN PATENT DOCUMENTS

| | | |
|---|---|---|
| EP | 1457764 A1 | 9/2004 |
| EP | 2546636 A1 | 1/2013 |

(Continued)

OTHER PUBLICATIONS

International Search Report regarding PCT/SE2015/000010, ISA/SE, Stockholm, dated Jul. 10, 2015.

(Continued)

*Primary Examiner* — Dennis White
(74) *Attorney, Agent, or Firm* — Harness, Dickey & Pierce, P.L.C.

(57) ABSTRACT

A printed gas sensor, comprising a metalloporphyrin dye, has first and second modes, and a nanoporous carrier material comprising a plurality of particles measuring less than 5 µm; the particles have a plurality of pores, the pore size in the range 5-50 nm, wherein the metalloporphyrin dye is bound to the nanoporous carrier material. The disclosure further comprises a method of preparing a gas sensing composition for detection of food status and a digital expiry date device system, which comprises a packaging material with inner and outer surfaces; a first transponder disposed on the inner surface and a second transponder disposed on the outer surface. A sensor portion is electrically connected to the first transponder for detecting food status and communicating the status to the second transponder. The sensor portion comprises a metalloporphyrin dye which configures an impedance change upon binding with an gaseous analyte, and a printed numerical array.

8 Claims, 5 Drawing Sheets

(51) Int. Cl.

| | |
|---|---|
| *G06Q 10/08* | (2012.01) |
| *G01N 27/12* | (2006.01) |
| *G01N 33/00* | (2006.01) |
| *G01N 33/02* | (2006.01) |
| *G09G 3/19* | (2006.01) |
| *G06F 3/14* | (2006.01) |
| *G09G 3/20* | (2006.01) |
| *G06F 3/147* | (2006.01) |
| *G06F 3/041* | (2006.01) |

(52) U.S. Cl.
CPC ......... *G01N 33/0036* (2013.01); *G01N 33/02* (2013.01); *G06F 3/14* (2013.01); *G06Q 10/087* (2013.01); *G06Q 10/0832* (2013.01); *G06Q 50/28* (2013.01); *G09G 3/19* (2013.01); *G09G 3/2003* (2013.01); *G06F 3/041* (2013.01); *G06F 3/147* (2013.01); *G09G 2370/16* (2013.01); *G09G 2380/04* (2013.01)

(58) Field of Classification Search
CPC .... G09G 3/2003; G09G 3/19; G09G 2370/16; G09G 2380/04; G06Q 10/087; G06Q 10/0832; G06Q 50/28; G06F 3/14; G06F 3/041; G06F 3/147
See application file for complete search history.

(56) References Cited

FOREIGN PATENT DOCUMENTS

| | | |
|---|---|---|
| GB | 2361064 A | 10/2001 |
| GB | 2419868 A | 5/2006 |
| SE | 1330050 A1 | 11/2014 |
| WO | WO-2007004948 A1 | 1/2007 |
| WO | WO-2010066273 A1 | 6/2010 |

OTHER PUBLICATIONS

Written Opinion regarding PCT/SE2015/000010, ISA/SE, Stockholm, dated Jul. 10, 2015.

100

2014-10-03

3 day(s) left

0 day(s) left

FIG. 6B

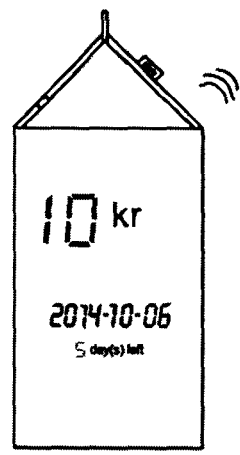
FIG. 7A
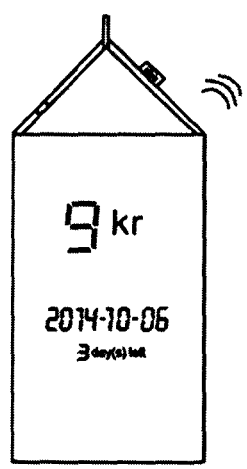  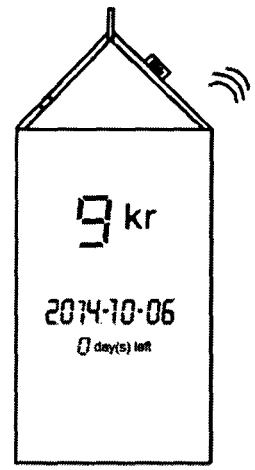
FIG. 7B     FIG. 7C ical Field

PRINTED GAS SENSOR AND DIGITAL EXPIRY DATE THEREOF

PRIORITY CLAIM

This application claims priority to the Swedish patent application no. 1430023-0, filed Feb. 24, 2014, which is incorporated by reference in its entirety.

TECHNICAL FIELD

This invention pertains in general to the field of transponder-to-transponder communication. More particularly the invention generally relates to printed gas sensors having a metalloporphyrin dye color change and machine-to-machine devices thereof, in particular food status sensors, in some embodiments.

BACKGROUND ART

This section is intended to introduce the reader to various aspects of art that may be related to various aspects of the present disclosure, which are described and/or claimed below. This discussion is believed to be helpful in providing the reader with background information to facilitate a better understanding of various aspects of the present disclosure. Accordingly, it should be understood that these statements are to be read in this light, and not as admissions of the complete prior art. The best before date is a date that does not describe the time for a food product to be edible, but a date that the food product is expected to retain its qualities such as taste, color, crispiness, elasticity and mastication. When a food product has passed the best before date, the quality of the food gradually becomes worse, but the food may still be fully edible. Best before dates are applicable if the product has been stored properly. Often information on proper storage is included on the container. The expiration date applies to unopened packaging, but also an opened package can keep after the expiration date. Expiration date is used on food products deemed by the manufacturer to deteriorate rapidly and become a health hazard. That is the expiration date is the last day on which the manufacturer can guarantee that a food product can be consumed without any danger to health. Methods for labeling of expiration dates and best before dates is conventional black printing ink— often printed in small font for the consumer to discern these dates.

Packaged foods products often become waste because of uncertainty about if the food is spoiled or not. There are no quantitative means to determine if packaged food is spoiled in the food chain. One of the great problems of mankind is to feed a growing population on with a limited supply on earth. In the twentieth century's later half, enormous progress in agricultural productivity was made, particularly in the third world. Today the development has stagnated and attention is directed towards the losses in later stages of the food chain. In the developed world, it is estimated that as much as 30% of the food go to waste, either because we can not manage to eat it, or because it is unfit to eat or sell. The global food wastage contribute to double of the carbon emissions of global air traffic.

In the following known means for alleviating the above problems will be described:

A time-temperature indicator that that is configured as a bar code is described by EP1901925B1 (Tempix AB).

3M's MonitorMark is an indicator with the that uses diffusion to provide a time-temperature indicator.

VITSAB's time temperature indicator is based on a color shift from enzymatic hydrolysis of a lipid substrate.

Lifelines Inc.'s color indicator FreshCheck is based on a polymerization reaction that leads to a colored polymer.

TimeStrip's indicator shows a coloring effect for a time lapse from pressing a button.

Insignia Technologies' indicator shows a coloring effect over a large color interval of brown, orange, violet upon exposure to UV-light and opening of a package.

FreshController—is a visual indicator that shows the freshness of a package after a package has been opened. This by a time lapse effect by a diffusion mechanism.

Even if all these technologies have been successful in their respective fields, they are too expensive compared to the benefits and would increase the cost for the products that they are applied to. Therefore, there's limitations of using these indicators or sensors for a large food product segment at low cost for food products with low margins and general food products. Furthermore, the indicators competes with the best before dates.

A freshness indicator is disclosed in WO03087955, in which the indicator provides easy determination if a food product is still suitable for safe consumption after a certain time has elapsed from the date the package is first opened and/or unpacked. The indicator comprises a programmable controller with a separate power source in combination with at least one display means and/or at least one audio element. There is at least one sensor and the timer for the indicator. The document also discloses that the sensor is triggered by an external means. The invention can be used for a package.

The patent application FR2809519A discloses a method and apparatus for controlling the freshness of the products that are perishable after opening a package. The device consists of a housing with an optical reader of bar codes, a memory, an internal clock, a counter, a display and keys. The device can identify the product, with respect to storage conditions calculate and suggest to the consumer a new expiration date earlier with regard to the opening of the package.

In the application WO2001082006A1 a technology for a consumable expiration date indicator is disclosed characterized in that it comprises a thermal paper or an iridescent temperature sensitive material which is controlled by a circuit or integrated circuit for indicating a predetermined expiry date visually and automatically. The invention essentially comprises a thin patch that may be secured or attached to the packaging of an area which clearly changes color. The document also describes that an LED can be used to change brightness when the predetermined expiry date is reached.

The application WO2006032834A1 describes a timer unit to monitor the time period associated with foods and other substances with a finite time as these are suitable for use. The timer unit is programmable by a user to monitor a plurality of time periods, where each time period is identified by a unique code as an alphanumeric code. The tags can be attached to a product such as a lid to a food jar, and its identifiable code can be entered on a keypad on the timer unit so that the period during which the tag is attached can be controlled and can be read at any time during the default period during which product in the can is edible. The device helps to ensure the safe use of food products and reduces product waste.

Furthermore, the patent application U.S. Pat. No. 5,802,015A describes an electronic timer label to indicate the end of a period associated with a specific article. The label comprises a pulse generator and a binary counter. The pulse generator is configured to generate a series of pulses at a predetermined pulse, and the counter is configured to count from an initial count in response to the series of pulses and for generating an output signal on attainment of a final count. The label also includes a display that indicates the end of the time period, a programming port to control the programming pulses to the counter, and a mechanism to affix the label to a surface of a product.

The patent application WO2007/064541 describes an electronically printed chromatic elapsed time indicator device comprising a switch, a power source and a voltage-driven elapsed time display means for displaying the elapsed time in the activation of a switch and regardless of the actual date of activation thereof. The components are functionally connected to each other and are printed on at least one substrate.

The patent application US2004/156418A1 describes an electronic time-temperature indicator that may appear in a label indicating that the time or temperature levels have been reached which may jeopardize the quality, durability, or safety of the item label is arranged on. The label can be used on a variety of items that require careful handling when it comes to temperature and/or time elapsed before use. The label may be in the form of a flexible, disposable label that usually is powered by a small battery.

The patent application GB2344101A discloses a timer device which comprises an electrochemical structure which provides a visual indication of elapsed time.

The patent application GB2443486, discloses an attachable, reusable electronic device that counts the days of storage of perishable goods. The device measures a time from when a fresh product is exposed to air upon opening or breaking a package. It may also include a flashing warning light to indicate when one day remains. The unit can be connected to the goods themselves. The unit is programmed by the user or have a preset time. The patent EP2390203B1 describes a package that has a wall with a sensor on the inside of the package and an antenna on the outside of the package to communicate information about the contents of the package with the antenna on the outside of the package. The package wall is an electrically conductive layer extending between the inner side and the outer side to communicate information about the contents of the transponder on the outside of the package to an external transponder reader. The problem with the technology is that the electrical connection between the inside and the outside of the packaging is very difficult to achieve in practice for most food packages.

It would be very useful for the art if an alternative to conventional expiration dates and best before dates of packaging could be provided to reduce food wastage. To meet the need of a packaging indicator for increased food safety and reduced food wastage, it would be desirable to provide a food status indicator with relatively inexpensive components. The color change of the indicator would also need to be reliable in order to replace conventional best before dates, otherwise there is a risk that the consumer gets confused by mixed messages.

The present invention eliminate, prevent or overcome the aforementioned problems of the prior art, which would be a step towards the application of food status sensors in the food supply chain having the features in the appended claims. The present technology solves the problems of the conventional best before date, whose drawbacks have led to the art of color indicators. Furthermore, the present technology seek to solve problems of using an electrical connection from a sensor on the inside of a package to the outside to detect the status of the food inside of the package.

SUMMARY OF THE INVENTION

The present invention relates generally to machine-to-machine sensor communication. In some cases, embodiments of the invention relate specifically to providing food status indication by means of a gas sensing chemical sensor.

Accordingly, an object of the invention, in some embodiments, is to provide a digital expiration date that can replace conventional printed expiration dates. It is also an object of the invention to provide digital expiration date devices to make it easier to determine whether a food product is still edible and to increase the food safety for the food consumer. To achieve these and other advantages and in accordance with the purpose of the present invention, as embodied and broadly described herein, there is provided a chemical gas sensor as defined in claim 5. Disclosed herein are also further examples of the disclosure, all related by the chemical gas sensor, to provide for e.g. machine-to-machine communication of sensing information.

According to a first aspect, a method of preparing a gas sensing composition is provided, comprising; diluting a metalloporphyrin dye in solvent to a concentration of 2-20 mg/mL; dissolving a nanoporous carrier material in said solvent; mixing said diluted metalloporphyrin dye with said dissolved nanoporous carrier material, wherein said nanoporous carrier material having a pore size in the range 5-50 nm and a particle size less than 5 μm; and evaporating said solvent from said nanoporous carrier material for binding of said metalloporphyrin dye to said nanoporous carrier material.

In a second aspect, a printed gas sensor is provided, comprising;
a metalloporphyrin dye having a first and a second mode, said first mode having the Formula I;

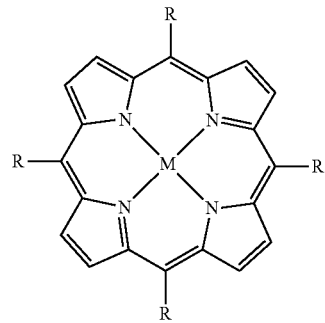

Formula I wherein M is a metal ion and R is alkyl or aryl, and wherein said metal ion is chosen from the group $Sc^{3+}$, $Zr^{4+}$, $Lu^{3+}$, $Cr^{3+}$, $Mn^{3+}$, $Fe^{3+}$, $Co^{3+}$, $Mo^{5+}$, $Ru^{2+}$ and $Mg^{2+}$; a nanoporous carrier material comprising a plurality of particles with a size less than 5 μm, said plurality of particles having a plurality of pores with a pore size in the range 5-50 nm, wherein said metalloporphyrin dye is bound to said nanoporous carrier material, said nanoporous carrier material having a first color in said first mode and a second color in said second mode upon ligation of an analyte, preferably wherein said metal ion having a halide counter ion such as chloride.

In a third aspect, a digital expiry date device system is provided comprising; a packaging material having an inner surface and an outer surface; a first transponder disposed on said inner surface and a second transponder disposed on said outer surface; a sensor portion (155) electrically connected to said first transponder for detecting food status and communicate said status to said second transponder (130), wherein said sensor portion (155) comprises a metalloporphyrin dye to configure said sensor portion for an impedance change upon binding of a gaseous analyte to said metalloporphyrin dye, wherein said second transponder (130) comprising a writeable and readable digital medium for storing data of which of said numerical segments to be configured in said first mode (112a) and said second mode (112b), wherein said second transponder is arranged on said substrate (101) electrically coupled to said integrated display driver circuitry (120), wherein said plurality of digit segments are configured for said writable and readable digital medium with said transponder (130); a printed numerical array (102) comprising a plurality of said digit segments (112a, 112b) disposed on said substrate (101) for providing a variable expiration, wherein said plurality of digit segments (112a, 112b) have a respective first illuminated or colored mode and a second colorless mode; an integrated display driving circuit (120) disposed on said substrate electrically connected to said plurality of digit segments for logical switching to said first or said second mode, wherein said plurality of digit segments are configured for the expiry of a perishable product, and wherein said second transponder (130) measuring an impedance greater than a threshold for edible food said at least one digit is displayed that includes 2-7 of said plurality of digit segment of said first mode, preferably wherein said substrate (101) comprises an adhesive surface for attachment on the outside of a package.

In the following advantages of the invention will be described:

The technology can replace or supplement the best before date and provide real-time information on food status. If the sensor is integrated on a platform for printed electronics one obtains a product with potential for handling large amounts of information and traceability of food throughout the value chain—from production to consumption.

Another advantage of the invention is that information on food status and traceability reduces the large food waste throughout the value chain, to achieve a more sustainable food handling and increased cost effectiveness.

An advantageous feature of the technology is that it provides a method to detect and quantify the degradation processes of food, which is not influenced by history at the food handling: transport, storage, cold chain, temperature variations, etc.; without measuring directly and irreversibly microbial activity and the degree of degradation in real-time. Customer benefits from the use of this product is a direct, reliable and cost-effective measurement of food quality and status over time, where the sensor may be a simple, visual indication of the status e.g. prior to purchase or consumption. Different actors can quantify this status from production to consumption as a basis for action. Existing solutions (in addition to the established rule about the best before date) is based primarily on indirect measurement by temperature variations in a food cold chain, which only gives an estimate of the food status (equivalent to a 'best before date'). Such estimation is based on prediction models to correlate temperature history indirectly related to bacterial growth, which will probably not lead to better control to reduce food waste.

Advantageous features of the invention for end users in the food supply chain (consumers) are: easier handling of food and broken containers in the fridge, better control of food status than the best-before date, secure purchases of food and integrated functionality with mobile phones.

Advantageous features of the invention in the food supply chain for producers, distributors, wholesalers and retailers of food are: improved logistics and efficient administration of the production, transportation, warehousing, inventory, and pricing.

Advantageous features of the invention in the food supply chain for the food and packaging industry are: reduced negative environmental impact of packaging, and proactive management of the issues surrounding food waste to avoid regulatory requirements.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 6A shows a digital expiration date device 100 in an enlightened or colored state;

FIG. 6B shows a digital expiration date device 100 in an enlightened or colored state;

FIG. 7A is a schematic view of a package 140 that with an integrated digital expiry date device 100 on the outside of a package;

FIG. 7B shows a schematic view of the package 140 of FIG. 6A;

FIG. 7C shows a schematic view of a package 140 that comprises an expiration date device 100 on the outside of the package that provides a digital expiration date.

DETAILED DESCRIPTION OF THE INVENTION

Figure 1:
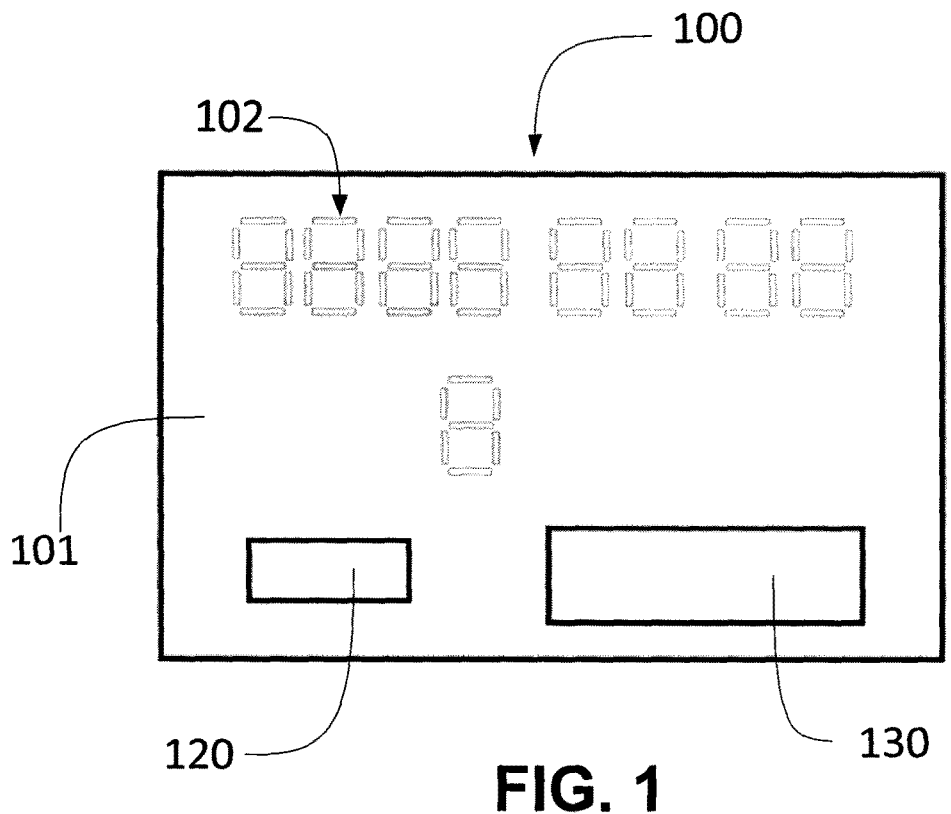
FIG. 1 is a schematic view of a digital expiry date device 100 viewed from above with an uncolored numerical array 102.

Specific examples will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements. The invention will be described in greater detail below by way of illustration of embodiments with reference to the attached drawings, in which:

FIG. 1A is a schematic view of a digital expiry date device 100 viewed from above with an uncoloured numerical array 102. It is further possible that a display means may include electrochromic cells with red pigment coupled to a transponder, with the green pixels of a second transponder, and that the display means comprises electrochromic cells with blue pigments electrically coupled to a third transponder in which each of said first, second and third transponders receives a code in the form of a binary matrix for which of said electrochromic cells that should be configured in the second colored state for an image on the display device 100 in the RGB color scale.

Figure 2A:
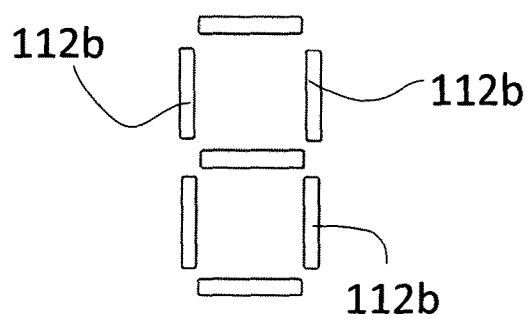
FIG. 2A shows a schematic view of a plurality of digit segments (112a, 112b) in 7-bit segment sets for providing digital numbers.

FIG. 2A shows a schematic view of a plurality of digit segments (112a, 112b) in a 7-bit segment set for providing digital numbers. Numeric segments displayed in a colored 112b mode.

Figure 2B:
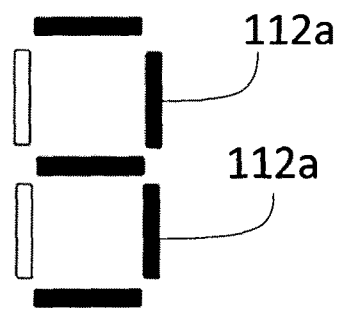
FIG. 2B shows a schematic view of a plurality of digit segments (112a, 112b) in an illuminated or colored state.

FIG. 2B shows a schematic view of a plurality of digit segments (112a, 112b) in an illuminated or colored position where 5 digit segments are enlightened or colored to provide the number 3 to a user.

Figure 3:
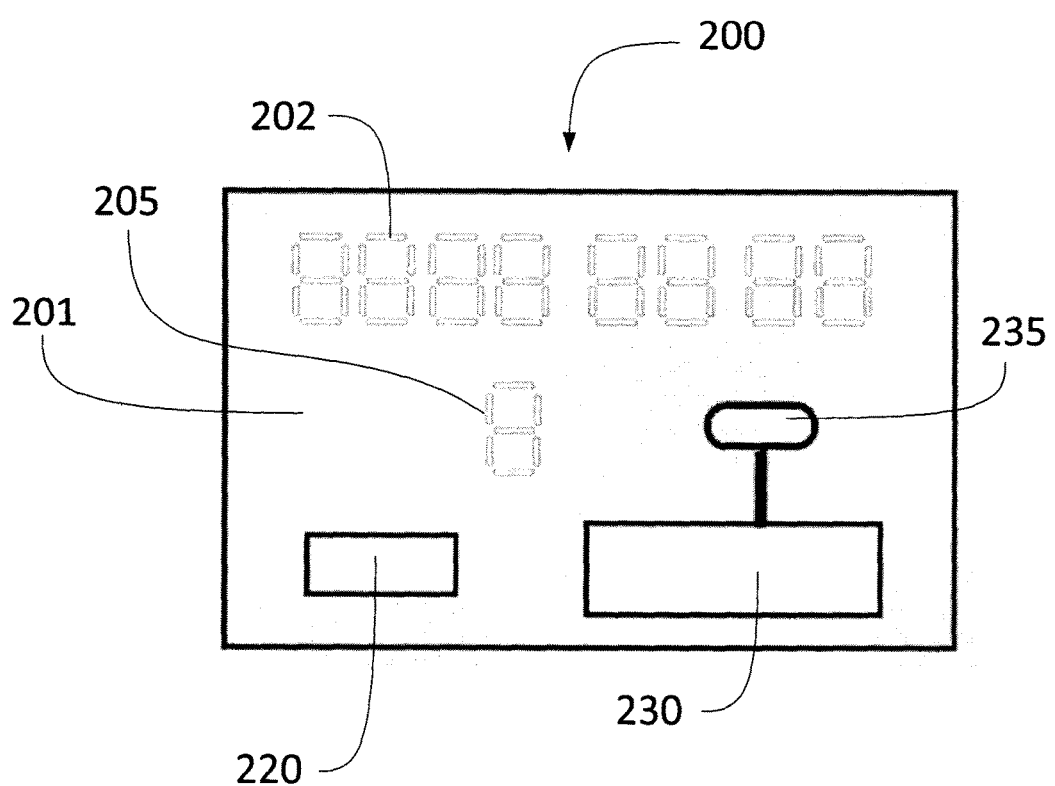
FIG. 3 shows a schematic view of a digital expiry date device 200 viewed from above with an uncolored numerical array 202 that includes a printed gas sensor for detecting the expiration date of a perishable food product.

FIG. 3 shows a schematic view of a digital expiry date device 200 viewed from above with uncolored numerical array 202 that includes a sensor for detecting the expiry of perishable goods. An advantageous feature of the printed chemical gas sensor with metalloporphyrin dye is that the technology can be used for a wide range of food at various temperature such including room for food packaging. Another advantageous feature is that bulk detection of food-borne bacteria.

Figure 4:
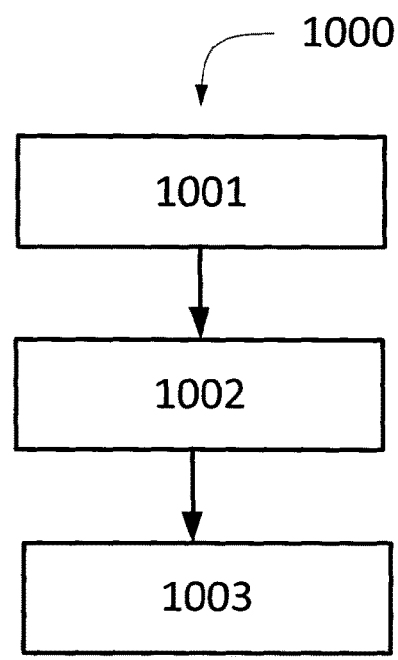
FIG. 4 shows a schematic view of an embodiment of the invention to provide a digital expiry date device on a food package.

FIG. 4 shows a schematic view of an embodiment of the invention That provides a digital expiry date on a package for communicating sensory information from the inside of a package through the wall of the package 140 to a transponder on the outside of the package 140.

Figure 5:
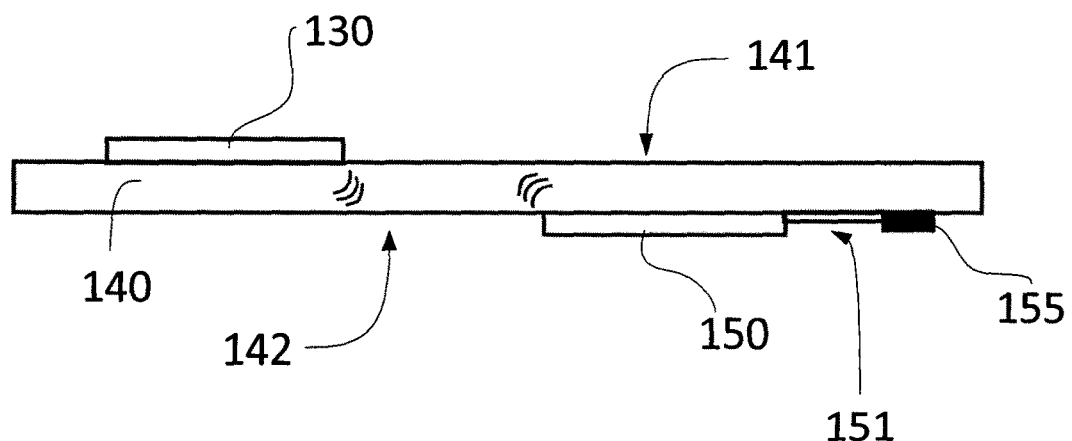
FIG. 5 shows a schematic view of a wall of a package (140) in cross section with transponder-to-transponder communication.

FIG. 5 shows a schematic view of a wall of a package 140 in cross section where a first transponder 130 is arranged on the outside 141 of the package to be displayed to a user, and a second transponder 150 is arranged on the inside 142 of the packaging with an electrical connection 151 from the transponder 150 to a sensor portion 155 for detecting the food status inside the package. It is preferred that the sensor portion 155 comprises iron(III) porphyrin and a nanostructured material with a high surface, for example where the area is e.g. 2000 m$^2$/g. Bacteria start growing in carbohydrate rich food after a time that depends on food type and environmental conditions. When the oxygen level decreases for food enclosed in food packaging, bacteria produce a wide range of various bacteria metabolites. The various bacteria metabolites from spoiled food can be detected chemically, since they have reasonably high vapor pressures. The vapor molecules from bacteria bind chemically to dye molecules in the sensor. As the bacterial colonies grow on the food surface, the amount of reacted dye molecules increases with time until the indicator is saturated. A color shift of the label occurs at a lower concentration than a concentration that is detectable by smelling. According to embodiments of the chemical printed sensor, it is preferred to detect various acids from bacteria in decayed food chemically by iron porphyrins. For example, lactic acid has a vapor pressure of 0.01499 mm Hg at 25° C. The acids from bacteria bind chemically to iron porphyrin in the sensor layer. When bacterial colonies grow on the food surface to increase the proportion of reacted metalloporphyrins until the sensor portion 155 is saturated. The impedance of the sensor is measured by the transponder 150. When the bacterial colonies have grown to a threshold level, a measurable impedance change of the sensor portion 155 is detected at a certain concentration of carboxylic acid where the carboxylic acids are bound to metalloporhpyrin dye resulting in the impedance change. It is preferred that a layer of ink is printed on the inside 142 of a package 140 for providing an electrical signal into contact with the food atmosphere in a sealed package. The impedance of the sensor portion 150 due to the high electronegativity and surface area for the ironporphyrins where the reaction rate increases with a higher surface area. It is preferred to detect any of the two biomarkers for detection of food status are carboxylic acids formed in bacterial metabolism and alkyl amines formed during lipid oxidation in meat and fish. The iron in iron porphyrin is seated in a porphyrin ring. Iron has the orbital structure $1s^2\ 2s^22p^63s^23p^64s^23d^6$. The iron has 5 d-orbitals $d_{xy}$, $d_{x2}$, $d_{y2}$, $d_{x2-y2}$ and $d_{z2}$. The binding of ligands occurs by the $d_2{}^2$ orbitals perpendicular to the porphyrin ring plane. The color shift of the porphyrin is due to changes in the Soret band optical transitions upon ligation with the d-orbitals with pi-symmetry species. The ligand becomes ligated axially. Carboxylates bind to the iron with hydrogen ion as a counterion. The Soret band is influenced by the ligand binding, i.e. π-π* transitions for the porphyrin is affected, which causes the color shift. Absorption wavelengths have peaks in the range of 400-440 nm, but the color that is seen is due to the reflected light.

The digital expiry date may be embodied as a QR code with switching of electrochromic cells that comprises information of an expiration date. Electrochromic cells may change color by means of a binary message where the electrochromic cells are printed on the substrate. The electrochromic cells can cover a larger area of the substrate and be pre-configured as images. When the transponder is activated, a voltage increases over the electrochromic cells so that the electrochromic cells change color. An electrochromic dye can be used for an electrochromic cell that can change color from white to blue for example, where the dye is etylvilogen, but is only one of many electrochromic dyes. One advantage of the embodiment is that it is possible to configure nuances with the voltage level from a transponder. Furthermore, according to aspects of the present disclosure, without any intention of limitation, a message is sent to transponders with code A to configure display means according message X, with which the display means or pixels are activated for displaying an image according message X. The message X is preferably a code corresponding to a matrix of image B. It is preferred to configure the display means' colors according to a message that corresponds to a binary matrix of an image in which each display means colors' are shifted by pixels according to the RGB system for added color mixing and where the transponder configures field effect transistors' electric modes so that they are turned on or off as a digital 0: a respective digital 1 to control the color of each pixel. The binary matrix may comprise 3D stereographic data.

FIG. 6A shows a digital expiration date device 100 in an enlightened or colored state where a digital date 2014-10-03 provided on the expiry date device. The expiry date is a best before date and a counter shows that 3 days remaining until the expiration date is reached without user interference. It is preferred that an algae battery can power both an active transponder and the drive circuit 120 of the numerical array, but it is preferable that the transponder 130 on the outside is passive and not driven by a battery. FIG. 6B shows a digital expiration date device 100 in an enlightened or colored state where the date 2014-10-6 is an expiry date. A counter shows "0" days remaining until the expiration date is reached. The passive transponder may be printed and configured with a pole placement so that the power from the transponder is reflected by a mismatch of the resonance frequencies through an impedance change by $$\Gamma = \frac{Z_L - Z_s}{Z_L + Z_s},$$

$$P_{transponder} = P_t G_t G_r \left(\frac{\lambda}{4\pi d}\right)^2$$

$$P_{reflected} = P_{transponder} \cdot \Gamma(\omega)$$

$$P_{transponder} = P_t G_t G_r \left(\frac{\lambda}{4\pi d}\right)^2 \Gamma \cdot G_t G_r \left(\frac{\lambda}{4\pi d}\right)^2 = P_t G_t^2 G_r^2 \left(\frac{\lambda}{4\pi d}\right)^4 \cdot \Gamma(\omega)$$

The pole placement of the reflected frequencies are determined by a printed RLC circuit with poles poler $$\omega_0 = \frac{1}{\sqrt{LC}}$$

i.e. physical encoding. The reflected power provides a reduction of power at the frequencies $\omega=\{\omega_1, \omega_2, \ldots, \omega_n\}$ which is detected by the transponder on the outside of the package.

FIG. 7A is a schematic view of a package 140 with an integrated digital expiry date device 100 that is visible on the outside of the package. The figure shows a price "10" kr where the number "10" is configured through wireless communication between a transponder in the digital expiry date device.

FIG. 7B shows a schematic view of the package 140 of FIG. 6A where the price is reduced through wireless communication between an external transponder reader and a transponder of the digital expiry date device when only "3" days are left until the best before date.

Further, according to an aspect of carrying out the invention in its scope, without any intention to be limiting, two transponders communicates through a package wall from the inside 142 and outside 141 or vice versa. A printed transponder 150 may be an electric circuit which is electrically connected to a dipole antenna with the impedance of a printed sensor portion 155 for detecting the consumption status on the inside 142 of the package and communicate this to the transponder 130 on the outside of the package 141. A transponder 150 may be printed with an electrical connection 151 to a sensor portion 155 on the inside 142 of the package 140. The sensor may be configured for binding of gaseous metabolites from food-borne bacterial metabolism, i.e. the metabolites carboxylic acids; such as acetic acid or lactic acid; or alkyl amines that can serve as biomarkers of degradation processes in food. The porphyrin-silica material may be prepared as an ink in the form of a liquid or colloidal suspension. The indication of the status of the food is done by a color change, where the binding of the metabolite to porphyrin to a change in the ink absorption spectra. It is preferred that the color change may be read visually or optically by photometry. The ink electrical characteristics is changed upon binding which is proportional to an impedance change.

FIG. 7C shows a schematic view of a package 140 with an integrated expiration date device 100 on the outside of the package that provides a best before date "2014-10-06". The package 140 shows a reduced price of the product when the counter shows the number of days '0' to go until the best before date "2014-10-06".

A method according to the invention is a method of providing an analyte sensing ink formulation, comprising; mixing of metalloporphyrin dye diluted in solvent with a nanoporous silica carrier material having a pore size in the range 5-50 nm and a particle size less than 5 µm; evaporating the solvent, preferably at room temperature. The mixing of said metalloporphyrin dye and said nanoporous material is performed in the presence of aluminium foil and/or in an aluminium covered container.

In some embodiments, a binary message may be sent to a transponder to configure an expiration date. The digital expiration can be provided by the bacterial growth time for food using the impedance of the printed gas sensor as a signal for the bacterial growth.

In some embodiments, the nanoporous silica material synthesized using the fumed silica Cab-O-Sil. The metal ion is iron for binding of carboxylic acids from bacteria and/or alkyl amines from lipid oxidation for detection of food status and/or for detection of bacteria from an infected wound. In some cases, the metal ion may be magnesium for detection of alcohol vapors for providing information of fruit ripening and/or for providing a physical restriction of operation of a car by detection of alcohol from the breath of a driver. In some embodiments, the nanoporous material is a silica with MCM-41 structure and having a pore size of 3.5 nm.

In some embodiments, the expiration date device communicates with a transponder sensor inside a package. Identification codes for the package type can be stored in an expiration date units by means of a transponder for writing and readable digital media. A user can read the transponders with a transponder reader in their mobile phone to automatically generate a shopping list in his or her cell phone. Information on packages can be displayed on the mobile phone screen after a user has read the transponders of the packages, which are shown in a hierarchy from the cheapest to the most expensive on the mobile phone's display screen. In some examples, the information about each corresponding package available in a store, may be displayed on a map on a screen for the user to locate the mentioned type of packaging.

The description above provides examples of how the expiry date device 100 provides a digital date on a substrate which may be a label 101 mountable on a package 140. A preferred manufacturing process for such labels or substrates is roll-to-roll processes using a flexible substrate 101 that can be reused in multiple machines or roll-to-roll processes where the substrate can be a packaging material, but should not be considered limiting.

A fridge that comprises an internal or eller external transponder reader may be used with a touchscreen to provide expiry dates on the touchscreen. A counter may show zero remaining days of use or in red. A digital expiry date can be shown in green and a counter of remaining days to expiry may show the remaining days a product is edible. The counter may be configured by the voltage level of electrochromic cells.

In some embodiments, the gas sensor (155) may include an iron(III) porphyrin to configure the aforementioned sensor portion of an impedance change upon binding of a gaseous bacteria metabolites. In some cases, the numerical array may be arranged to display a digital counter, preferably the number of days of remaining consumption for a food product or a drug. A price or an expiration date may be configured with the plurality of digit segments. A second transponder (150) may comprise a printed antenna.

In some embodiments, the numerical array is manufactured as a printed light-emitting diode array or an array of electrochromic cells arranged as 7-bit numbers because the transponders have a limited writing and readable memory for controlling a display. In some embodiments, the electrochromic digit segments are manufactured as a print on a label 101.

The transponder 130 is activated by voltage over a digital driver circuit 120 for the electrochromic cells, upon digit become enlightened according to a message sent to the transponder 130. An electrochromic dye may be used for an electrochromic cell that can change color from white to blue for example, where the dye is methylvilogen, but is one of many electrochromic dyes.

Hereinafter, methods and recipes of preparing gas sensing ink and will be described.

Example 1 Preparation of Gas Sensing Metalloporphyrin Ink Component—Best Mode

The nanoporous silica MCM-41 with hexagonal pore structure and a pore size of 3.5 nm was purchased from GREEN STONE SWISS CO., LIMITED No. 106, Houdaixi Road, Xiamen, China in containers of 2×50 g for $148. All other chemicals were purchased from Ramidus AB. The iron porphyrin as-used is 5,10,15,20-Tetrakis (pentafluorophenyl)-21H, 23H-porphyrin iron (III) chloride [4] that was purchased from Sigma-Aldrich in a quantity of 100 mg. The iron porphyrin was dissolved in a total of 500 ml toluene split on two bottles with one bottle having a lower concentration iron porphyrin than the other. The metalloporphyrin was obtained as a black solution from Ramidus AB with a concentration of 233 microgram/mL. The active substance was prepared as a blend of toluene, iron porphyrin and nanoporous material MCM-41. A batch of paste of the metalloporphyrin solution and nanoporous silica was prepared in an aluminium foil container. Approximately 10 g of white MCM-41 powder was poured into an aluminium foil container. Iron porphyrin toluene solution was pipetted with a peleus ball standard pipett. The blend was manually stirred with a spoon. The blend did not change viscosity due to mixing. The as-blended active substance was due to the high amount of silica added a paste. The paste was black when wet by toluene and was dried at room temperature for 1 day. Sensors were prepared by dissolving the dried green powder in a bit of water and depositing the colloidal solution on a paper substrate. Sensor areas were cut from the paper and were given names of a three letter prefix and a number suffix. As-prepared sensors were stored at room temperature and in a fridge and remained green at all times as-stored. Sensor areas of 1 cm$^2$ were prepared either prepared by pipetting iron porphyrin solution directly on paper or by depositing the dissolved green powder with a spoon. The prepared sensors was let dry in an aluminum foil container. Preliminary experiments with pipetting of iron porphyrin/toluene solution on paper and preparing sensors did not give any color change detectable by plain sight. A first set of sensors TK-1 were prepared with the ratio 5 g MCM-41 SiOx/50 ml Fe(TPP)Cl weak concentrated solution. A second set of sensors TK-2 were prepared with 10 g MCM-41/500 ml Fe(TPP)Cl solution. Flasks were cleaned, rinsed and then filled with approx. 5 cl as-purchased concentrated acetic acid. Acid vapor from the filled bottles was readily detectable by smelling. A lid was cleaned and rinsed, and a tape was folded and rolled as the adhesive towards a cut paper substrate with the deposited sensor. Pictures were taken before and after exposure. Bottles with sensor lids were stored in a fridge at 8 C for 1 day without intermediate checking of color shifts. After exposure to acetic acid for the storage period of 1 day, before and after pictures were compared. Sensors were stored in a fridge for 2 months after experiments and did not undergo a color change during that period i.e. the sensors were still green, however, experiments after storage in a fridge or freezer was not carried out. The sensor undergoes a color change upon exposure to acetic acid. It could be seen that the particles for the TK-1 sensors change color, but part of the paper remains green. The experiments were performed with difficulty of depositing the material on the paper, which explained the poor yield. The particles undergo a color change from dark green to dark red. Sensors were assumed to be fully saturated after exposure to acetic acid for 1 day upon which a color shift was demonstrated from pale green to red. The color shift from the evaporation of toluene was achieved directly upon adsorption or binding of metalloporphyrin to the nanoporous material or silica particles. The iron porphyrin must be attached to the silica for the heme, not to be toxic. The partial pressure of biomarker is expected to decline at a lower temperature such that the time before the sensor switches may be slightly longer. It is preferred that the ink formulation have no charged groups that may affect the affinity for binding the acid (bacterial metabolites) is preferable. Uniform coating of the active substance as a sensor ink may be tuned by rheological considerations. The metalloporphyrin dye is described by Formula I herein.

The color of the sensor can be modified by changing the pi-conjugated ring size. There's a total of 8 substitution positions on the porphyrin ring that can be used for substitution with aryl groups R.

Example 2 Preparation of Gas Sensing Metalloporphyrin Ink Component—Bad Mode

The iron porphyrin 5,10,15,20-Tetrakis (pentafluorophenyl)-21H, 23H-porphyrin iron (III) chloride was used for preparing a sensing ink reactive to acetic acid. Experiments were performed in a clean room class 10 at room temperature. All liquids and MCM-41 powder were handled in a fume hood. An amount of 0.2 g of MCM-41 was weighed in a 20 mL glass bottle, three samples were made one of them also containing aluminum foil. An amount of 10 ml Porphyrin-toluene solution was added to the glass bottles. The solution was then roughly shaken in a mechanic shaker and then sonicated (with ultrasound) for 5 minutes at maximum effect. To get an even solution. An amount of 40 micro liter of MCM-porphyrin-toluene was added to 10×10 mm plastic square wells, six samples in total. The samples were left to dry in a fume hood, three were named 51, 52, 53. The samples were brown when dry. To the other 3 samples 40 ul more were added to the same wells named 46, 47, 50. These were brown when dry. Chemical sensors 47, 50, 51, 52 were attached to a lid of a 60 ml plastic bottle containing 3 mL (covering the bottom with a few mm) 99% acetic acid. Sensors 53 and 46 were kept as references. After 19 hours the samples in over the acetic acid were compared with the references, showing no significant visual color difference. Two sensors were made with 1×40 microliter MCM-41-porphyrin-toluene, in the same way as for the previous samples. All samples were brown when dry. Ca 800 microliter mixture were set to dry on an aluminum foil, not comparing to a reference it looked green when fast dried on a heating plate (~50° C.). A glass container approx. 10 cm wide were covered with aluminum foil and the rest of the mixture with aluminum inside were poured in this and set to dry overnight inside the fume hood. After a time of 15-16 hours later the powder was compared to a reference and was then definitely brown. Some of the MCM-porphyrin-toluene solution from the evening (without foil) were added to a aluminum foil sheet at both the shiny side and the not-shiny side of the foil, in more or less randomly different constellations and let to dry. The result was brown-blackish color. Then two small petri-dishes (5 cm diameter) were covered with aluminum foil, and the MCM-41-porphyrin-Toluene solution were added, 1 mL and 0.5 mL respectively. The one containing less solution were let dry in room temp, and the other were set to dry at the heating plate (~50° C.). Both were brown when dried compared to both green and brown references.

| SAMPLE | COLOR AFTER PREPARATION |
|---|---|
| 18 ref TK2 | Pale green |
| 21 ref TK2 | Pale green |
| 46 | Red/Brown |
| 47 | Brown |
| 52 | Brown |
| 53 | Brown/Red |

Example 3 Concentration for Gas Sensing Ink

An amount of 0.2073 g MCM-41 was dissolved in 10 mL porphyrin-toluene mixture gives a concentration for MCM-41 of 20.73 mg/mL compared with earlier batches of 10 g MCM-41 per 500 ml of porphyrin-toluene conc MCM-41, 20 mg/mL. The new films (powder) becomes brown when dry and not green. The porphyrin concentration in more toluene was lowered but kept the same concentration of silica was giving a pale green print. The best mode for a gas sensing ink is in the range of 0.1 mg/mL-20 mg/mL. A more preferred range of concentration is 0.1 mg/mL-5 mg/mL. Furthermore, when aluminium foil was used hints of green could be seen but not otherwise.

Example 4 Drying of the Gas Sensing Active Powder

The as-prepared powder for preparing the gas-sensing ink powder may be spray-drying that has been considered as a bottom-up approach since it causes the possibility of designing functional materials with nanoscale properties of architectures in the size of microns from nanoparticles. Spray-drying is an already used method of preparing large amounts of dried powders for the food industry e.g. as powders for the chemical industry and the pharmaceutical industry. The method has been increasingly used for preparation of materials for controlled release of drugs in drug-delivery. Spray-drying has shown to produce micron-sized particles which are collapsed, donought-shaped, dispersed spherical shells, dispersed and agglomerated spherical solids in silica. Spray-drying has also been used to spray-dry mesoporous silica successfully into microspheres using surfactant. Nanocrystalline microspheres of an approximate size of 10 μm has shown to have a surface area of 560 m$^2$/g even without any template for mesoporosity. The synthetic conditions contributes to high temperatures due to the water content i.e. outlet temperatures needed is at least 100° C. A lower temperature is expected to improve the morphology of the particles. A donought shape form due to higher evaporation rates in the centre of the droplet, which is due to the higher temperature in the droplet centre. The gas supply is attached to the N$_2$-inlet and is heated up by an electric heater. A feed solution is pumped and sprayed through a nozzle.

Example 5 Modifications of the Metal Atom of the Metalloporphyrin Dye

| D-ORBITAL ELECTRONS | METAL ION | ANALYTE |
|---|---|---|
| 0 | SC$^{3+}$ | F$^-$ |
| 0 | Zr$^{4+}$ | F$^-$ |
| 0 | Lu$^{3+}$ | Salicylate |
| 1-7 | Cr$^{3+}$ | Salicylate |
| 1-7 | Mn$^{3+}$ | SCN$^-$ |
| 1-7 | Fe$^{3+}$ | Carboxylic acid |
| 1-7 | Co$^{3+}$ | O$_2^-$ |
| 1-7 | Mo$^{5+}$ | Salicylate |
| 1-7 | Ru$^{2+}$ | SCN$^-$ |
| N/A | Mg$^{2+}$ | Ethanol |

Example 6 Aging of Ink Formulation and/or Active Ingredients

An as-synthesized pale green powder was green after 1 year of storage at room temperature. Upon exposure to acetic acid after this storage, the indicator turned blue instead of red.

It should be clear that the specific embodiments described herein is not to be limiting of the full scope of the invention that herewith will be described:

In some examples, a user may use their cell phone that has an M-RFID reader to obtain information on the mobile phone display as macronutrients and ingredients for food in a food package.

In some examples, a packaging system detects that a food product contains a food-borne bacteria, which is communicated by transponder-to-transponder communication.

In some examples, information is sent automatically to a food manufacturer if a food product contains food-borne bacteria so that the food supplier can identify where all packages of the same food product has been sold, the price at which they were sold, sales date, expiration date, stock cooling and route upstreams the food supply chain.

In some embodiments of the gas sensor, the sensors are integrated in food packaging that communicates with an RFID refrigerator system for determining the edibility of food in a refrigerator. For instance, the RFID refrigerator system may provide display objects on a touch screen which indicates if a food package is edible. The user can also arrange display objects on the touchscreen in a sequence of expiration dates. The user can rearrange food in the fridge for different meals, and food packaging in the fridge may lit up for fetching ingredients according to a recipe.

In some embodiments, the printed gas sensor comprises an iron porphyrin dye for detection of food-borne pathogens. The pathogens that may be detected are *Listeria monocytogenes*, *E. Coli* or *Salmonella*. In some embodiments, the detection is displayed and communicated to a user by a refrigerator or cell phone.

In some embodiments, the printed chemical sensor is provided as a visual indicator for determining the edibility of the contents of a package printed as a single print layer on paper or plastics.

In some embodiments, the printed gas sensor is provided in a patch for diagnosis of wound infection or providing wound health to a user such that information of the status of the wound is provided to a patient or user.

In some embodiments, the printed gas sensor is integrated with a plurality of transponder configured display means, remote communication means, a cloud service and a plurality of servers in order to provide a service based on the detection of an analyte that the printed gas sensor is configured for by means of a metal ion center. The cloud service communicates sensing data to users' transponders electrically connected to the chemical sensor that comprises at least one metalloporphyrin dye.

In some cases, a user may rank different food products according to information from the expiry date of the units in a list on their cell phone by scanning packages with expiration dates devices via wireless communication.

In some examples, packaging with integrated expiry date devices is part of a system for automatic price changes that appear on the packaging. The pre-programmed expiration date can be sent to a transponder of a expiration date device. In some examples, a user can re-order expired food by reading the food labels that passed the expiration date of the user's refrigerator. In some examples, a digital expiration date on a pharmaceutical packaging is used to certify the authenticity of pharmaceutical packaging.

In some examples, a digital expiry date on a blood bag detects the status of the blood such as maintained cooling temperature.

In some cases, a self-service system is used where packaging is paid for by reading the packages expiration date for their prices with transponder readers where prices are configured for each respective package based on the number of days to the expiration date.

In some examples, digit arrays on digital expiry date devices are pre-printed electrochromic cells able to change color by regulating the voltage over the electrochromic cells.

In some examples related to aspects of the present disclosure, a pharmaceutical package may comprise a blood sampling unit comprising a substrate comprising a solid sharp mesoscopic capillary tube vertically onto said substrate. A pressure sensor may be provided at a lower portion of said mesoscopic capillary tubes and associated with a user pressing device with capillary tubes on a finger, a color change using LEDs or at least one electrochromic cell is provided as signal to a user that unit having a blood test. When the unit is pressed into the capillaries in the skin, blood is sucked into the capillary tube by capillary action and can travel to an area of analysis on the substrate through microfluidic channels. One way to prepare the said capillary tubes on the substrate for a minimally blood sample may comprise pressing polymer on said substrate as defined in a lithographic printing process. In one embodiment of said mesoscopic capillary tubes, spin-coating of polymer on a semiconductor wafer is used. Furthermore, a lithographically process such as NIL is used for producing a plurality mesoscopic holes in the said polymer layer, depositing an etchable structure having an upper surface and a lower surface of said polymer layer to lithographically define elongated mesoscopic tube in said etchable layer which has an inlet at the said top surface and an outlet at said plurality mesoscopic holes in said polymer layer. The polymer layer can be detached from said wafer and cut into a grid. The mesoscopic capillary tubes may also be etched on a plastic substrate.

In some embodiments, the printed gas sensor is used for detection of alcoholic levels allowed for driving providing a physical restriction to said car upon detection of alcohol in the breath from a person.

In some embodiments, the printed gas sensor is integrated in a disposable mouthpiece for breath alcoholic measurement. An RFID tag of the mouthpiece is configured by the alcohol level from the breath of a driver and read by an external RFID reader. It is preferred that the chemical sensor comprises Magnesium porphyrin.

In some embodiments, the chemical sensor is configured for binding of carboxylic acids from bacteria or alkyl amines from lipid oxidation of meat by iron porphyrin. The metal atom may be magnesium for detection of alcohol for a ripening sensor for fruit.

Preferred Embodiments

A preferred embodiment of the invention is a RFID refrigerator system for determining the edibility of food in a refrigerator comprising; a refrigerator that includes: at least one refrigerator door and an interior space, at least a touch screen, at least one RFID reader, at least a food package in the said internal space includes: an inside and an outside, an RFID tag comprising the said food outside of the package and a sensor surface of said food inside of the package, wherein said RFID tag comprises an electrical connection between the said sensor surface and said RFID tag, wherein said sensor surface has a first electrical position encoding an edible and/or drinkable content in said food package, and a second electric mode, which shows a non-eatable and/or drinkable content in the at least one food package, and wherein said RFID tag is configured to detect a level of bacteria metabolite vapor in the at least one food packaging above a threshold value by reading said RFID tag by the said RFID reader; and wherein said touch screen is arranged to provide a display area on the touch screen that displays on said at least one food package in said first electrical state, and wherein said touch screen is arranged to provide a display area on the touch screen which shows that the mentioned at least one food package in the said second electrical mode. For instance, the RFID refrigerator system may provide said display objects on the touch screen which indicates the at least one food package in said first electrical state, and provide said second display object on the touch screen that displays on the at least one food package in said second electric mode for arranging said display objects in a sequence of said touch panel after the expiration date, and whereby the user can configure the aforementioned display objects in a sequence. The said touchscreen may be adhered to the said refrigerator door, preferably magnetically. The sensor portion may comprise at least an ink layer on said inside of the food package. The sensor portion may be a printed ink comprising metalloporphyrins and a nanoporous silica having a substantially high surface area. At least one organic acid ligand may become substantially bound to said metalloporphyrin dye resulting in a change from the sensor position to the first electrical the second electrical state. The user can rearrange food in the fridge for different meals, and food packaging in the fridge may lit up for fetching ingredients according to a recipe.

Another preferred embodiment of the invention is a food status sensing device, is disclosed. The electrochemical food status sensor, comprises; a first electrode sheet, a printed ink comprising a nanoporous material that comprises metalloporphyrin for sensing of bacteria metabolites, a polymer electrolyte, a second electrode sheet, wherein said first electrode sheet is nanoporous for having a permeability to bacteria metabolite vapor exposure, a printed battery for providing a voltage over said electrochemical food status sensor; a printed display means for providing a visual signal of food status based on said bacteria metabolite exposure; an electrical circuit in electrical contact with said printed display means configured to lit said printed display means when said bacteria metabolite vapor exposure exceeds a threshold of 2-100 ppm.

A preferred embodiment of the invention is a spray comprising; a metalloporphyrin dye that comprises a metal atom, said metalloporphyrin dye having a first and a second mode, and said second mode for providing indication of food status; an aerosol dispersion that comprises particles in the size range 50 nm-1 micron, wherein said particles having a surface that is functionalized with alkyl groups and said metalloporphyrin dye is bound to said surface, wherein said metalloporphyrin dye preferably comprising aryl substituents that are not halogen substituted for high solubility in polar solvent. The metal atom may be magnesium for detection of alcohol from a breath and/or for detection of ripe fruit.

Another preferred method according to the invention is a method of producing an electrochemical food status sensor, comprising; providing a first electrode sheet; printing a solid polymer electrolyte on said first electrode sheet; printing an ink that comprises a nanoporous material and metalloporphyrin for sensing of bacteria metabolites on said polymer electrolyte; and providing a second nanoporous electrode sheet on top of said electrolyte.

Another preferred embodiment of the invention is a machine-to-machine food status sensing system is disclosed, that comprises; an electrochemical food status sensor that comprises; a first electrode sheet, a printed ink comprising a nanoporous material that comprises metalloporphyrin for sensing of bacteria metabolites, a polymer electrolyte, a second electrode sheet, wherein said first electrode sheet is nanoporous for having a permeability to bacteria metabolite vapor exposure; a voltage detector circuit in electrical contact with said electrochemical food status sensor for providing a voltage over said electrochemical food status sensor; a printed battery for providing a baseline voltage over said electrochemical food status sensor and said voltage detector circuit; a transponder in electrical contact with said electrochemical food status sensor, an RFID reader for reading said transponder for reading of said voltage over said electrochemical food status sensor for providing a measure of the food status of a food item.

Another preferred embodiment of the invention is a food spoilage sensing refrigerator is disclosed for providing a food spoilage warning for food spoilage sensing food packages in a refrigerator comprising: a refrigerator comprising a door enclosing an interior space, a transponder reader for reading transponders in food packages, a microcontroller electrically connected to said transponder reader and said display, a touchscreen for displaying the food status of a food package in said refrigerator on said touchscreen by reading the transponder. The microcontroller may be configured for displaying the food status of a plurality of food packages by degree of spoilage on said touchscreen. The microcontroller may be configured for displaying a warning upon detection of a food-borne pathogen. At least one pathogens are *Listeria monocytogenes, E. Coli* or *Salmonella* may be detected by the refrigerator.

Another preferred embodiment of the invention is a visual indicator for determining the edibility of the contents of a package comprising; at least one ink layer, wherein the ink layer is printed with an ink containing porphyrin further comprising at least one metal member and wherein the metal member comprises at least one binding orbital, in which the said packaging indicator has a first-color mode, which shows an edible and/or drinkable substance and a second color mode which indicates a non-edible and/or drinkable content, and comprising at least one nanostructured materials with substantially large surface in which at least a ligand is substantially axially bound to the at least one binding orbital of the metal member resulting in a change of the indicator first mode to the second colored mode. The indicator may be arranged on at least one surface and wherein the surface is part of a plastic lid, bag and/or plastic bag.

Another preferred method according to the invention is a method for diagnosis of wound infection, comprises; providing a machine-to-machine patch having a proximal and a distal surface, comprising a sensor reactive to bacteria metabolites on said proximal surface; providing a visual signal to a user by switching of display elements on said distal surface; electrically configuring said display element for providing visual status of wound infection and/or wound health to a user.

In a preferred embodiment of the invention a chemical sensor is provided that is prepared by a spray comprising; a metalloporphyrin dye that comprises a metal atom, said metalloporphyrin dye having a first and a second mode, for providing indication of food status; and an aerosol dispersion that comprises particles in the size range 50 nm-1 micron, wherein said particles having a surface that is functionalized with alkyl groups and said metalloporphyrin dye is bound to said surface.

According to another preferred embodiment of the invention a machine-to-machine-user system is provided, comprising; a plurality of transponder configured display means, a remote communication means, a cloud service comprising; a plurality of servers, a local scanning device, a service provider access, wherein said cloud service communicates sensing data to said user by said transponder wherein by a sensor comprising a sensor portion that comprises a metalloporphyrin dye.

Another preferred method according to the invention is a method of providing an alcoholic safety test for car usage, comprising; providing a mouthpiece comprising a first transponder; providing a car having a second transponder, configuring said car for an electrical signal from said sensor portion by wireless communication between said first transponder and said second transponder for providing a physical restriction to said car upon detection of alcohol in breath from a person.

Another preferred embodiment of the invention is a disposable mouthpiece for breath alcoholic measurement comprising; a disposable mouthpiece that comprises a sensor reactive to alcohol, a first transponder including a writable and readable digital medium for storing data of alcoholic content from the breath of a user, wherein said transponder measures an impedance greater than a threshold for alcoholic driving use, said electrical signal is communicated wirelessly to an external transponder for providing a physical restriction of operation of a car. The sensor may be a printed ink that comprises a metalloporphyrin dye. The metalloporphyrin dye may comprise any of the metal ion magnesium.

Another preferred embodiment of the invention is a machine-to-machine patch, comprising; a plastic sheet having a proximal and a distal surface; a sensor portion reactive to bacteria metabolite vapor disposed on said proximal surface for coverage of a wound, wherein said sensor portion comprising a metalloporphyrin dye that comprises a metal atom, preferably having partially filled d-orbitals; at least one display element disposed on said distal surface, wherein said display elements comprises at least one printed light-emitting diode or printed electrochromic cell; a display driving circuit disposed on said plastic sheet electrically connected to said at least one display element for switching of said display elements; a conductive connection penetrating said patch from said distal and proximal surface for providing a visual indication of wound infection and/or wound health to a user by said at least one display element. The proximal surface may comprise a nanoporous polymer for configuring the non-permeability of bacteria metabolites through said patch. The machine-to-machine patch may comprise a transponder electrically connected to said sensor portion for wireless communication with a transponder reader.

Another preferred embodiment of the invention is an RFID refrigerator system for determining the edibility of food in a refrigerator comprising;

a refrigerator that includes: at least one refrigerator door and an interior space, at least a touch screen, at least one RFID reader, at least a food package in the said internal space includes: an inside and an outside, an RFID tag comprising the said food outside of the package and a sensor surface of said food inside of the package, wherein said RFID tag comprises an electrical connection between the said sensor surface and said RFID tag, wherein said sensor surface has a first electrical position encoding an edible and/or drinkable content in said food package, and a second electric mode, which shows a non-eatable and/or drinkable content in the at least one food package, and wherein said RFID tag is configured to detect a level of bacteria metabolite vapor in the at least one food packaging above a threshold value by reading said RFID tag by the said RFID reader;

and wherein said touch screen is arranged to provide a display area on the touch screen that displays on said at least one food package in said first electrical state, and said touch screen is arranged to provide a display area on the touch screen which shows that the mentioned at least one food package in the said second electrical position.

The transponder refrigerator system may provide said display objects on the touch screen which indicates the at least one food package in said first electrical state, and provide said second display object on the touch screen that displays on the at least one food package in said second electric mode for arranging said display objects in a sequence of said touch panel after the expiration date, and whereby the user can configure the aforementioned display objects in a sequence. The said touchscreen may be adhered to the said refrigerator door, preferably magnetically. The sensor portion may comprise at least an ink layer on said inside of the food package. The sensor portion may be a printed ink comprising metalloporphyrins and a nanoporous silica having a substantially high surface area. At least one organic acid ligand may become substantially bound to said metalloporphyrin dye resulting in a change from the sensor position to the first electrical the second electrical state. The user can rearrange food in the fridge for different meals, and food packaging in the fridge may lit up for fetching ingredients according to a recipe.

Another preferred embodiment according to the present disclosure, is a machine-to-machine-user display system, comprising; a plurality of transponder configured display means, a remote communication means, a cloud service comprising; a plurality of servers, a local scanning device, a service provider access, wherein said cloud service communicates sensing data to said user by said transponder configured display means based on said user configuration, preferably wherein said display means are manufactured in a roll-to-roll process. The machine-to-machine-user interactive system may be an e-price tag system. The machine-to-machine-user interactive system may be a point-of-care system. The machine-to-machine-user interactive system may be an e-packaging system. The machine-to-machine-user interactive system may comprise a contact lens for providing diagnostic data to a user. The machine-to-machine-user interactive system may comprise a retail shopping system providing display data to a user. The machine-to-machine-user interactive system is a transponder-fridge providing display data to a user by a touchscreen.

Another embodiment according to the present disclosure, is a cellulosic pricing device, comprising; a cellulosic substrate having a top side for providing a displayed price and a bottom side, a transponder supported by said substrate, a bit number array comprising a plurality of display number bits electrically coupled to said transponder, wherein said plurality of display bits comprising; a printed transparent polymer electrode electrically coupled to said cellulosic portion soaked in a ionic liquid and in electrical contact to a printed polymer electrode on the bottom side of said cellulosic substrate, preferably wherein said top polymer electrode is poly(styrenesulfonate), wherein said cellulosic portion comprising a room temperature ionic liquid, and wherein said transparent polymer electrode is sensitive to the oxidation state of said ionic liquid for changing the color of said top electrode, wherein a set of said display bits are configurable as numbers by transmitting a binary message from an external transponder reader to said transponder.

A preferred method of the invention is a method of preparing a gas sensing ink formulation, comprising; (1101) diluting a metalloporphyrin dye in solvent to a concentration of 0.1-5 mg/mL; (1102) dissolving a nanoporous carrier material in said solvent; (1103) mixing said diluted metalloporphyrin dye with said dissolved nanoporous carrier material, wherein said nanoporous carrier material having a pore size in the range 5-50 nm and a particle size less than 5 µm; (1104) evaporating said solvent from said nanoporous carrier material for binding of said metalloporphyrin dye to said nanoporous carrier material. The nanoporous material may be a silica with MCM-41 structure and having a pore size of 3.5 nm. The solvent may be evaporated during spray-drying.

Another preferred embodiment of the invention is a printed gas sensor comprising; a metalloporphyrin dye having a first and a second mode, said first mode having the Formula I; wherein M is a metal ion and R is alkyl or aryl, and wherein said metal ion is chosen from the group $Sc^{3+}$, $Zr^{4+}$, $Lu^{3+}$, $Cr^{3+}$, $Mn^{3+}$, $Fe^{3+}$, $Co^{3+}$, $Mo^{5+}$, $Ru^{2+}$ and $Mg^{2+}$; a nanoporous carrier material comprising a plurality of particles with a size less than 5 µm, said plurality of particles having a plurality of pores with a pore size in the range 5-50 nm, wherein said metalloporphyrin dye is bound to said nanoporous carrier material, said nanoporous carrier material having a first color in said first mode and a second color in said second mode upon ligation of an analyte, preferably wherein said metal ion having a halide counter ion such as chloride. The nanoporous silica material may be synthesized using the fumed silica Cab-O-Sil. The metal ion may be iron for binding of carboxylic acids from bacteria and/or alkyl amines from lipid oxidation for detection of food status and/or for detection of bacteria from an infected wound. The metal atom or ion may be magnesium for detection of alcohol vapors for providing information of fruit ripening and/or for providing a physical restriction of operation of a car by detection of alcohol from the breath of a driver.

Another preferred method (1100) according to the invention is a method of preparing a gas sensing composition, comprising; (1101) diluting a metalloporphyrin dye in solvent to a concentration of 0.1-20 mg/mL; (1102) dissolving a nanoporous carrier material in said solvent; (1103) mixing said diluted metalloporphyrin dye with said dissolved nanoporous carrier material, wherein said nanoporous carrier material having a pore size in the range 5-50 nm and a particle size less than 5 μm; (1104) evaporating said solvent from said nanoporous carrier material for binding of said metalloporphyrin dye to said nanoporous carrier material. The nanoporous material may be a silica with MCM-41 structure and having a pore size of 3.5 nm. The solvent may be evaporated during spray-drying for increasing the surface area of said composition.

An other preferred embodiment of the invention is a printed gas sensor comprising; a metalloporphyrin dye having a first and a second mode, said first mode having the Formula I;

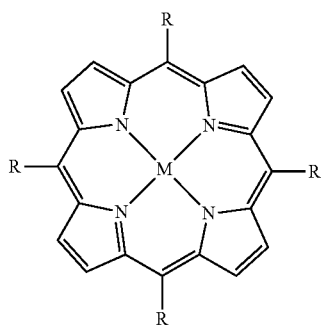

Formula I wherein M is a metal ion and R is alkyl or aryl; a nanoporous carrier material comprising a plurality of particles with a size less than 5 μm, said plurality of particles having a plurality of pores with a pore size in the range 5-50 nm, wherein said metalloporphyrin dye is bound to said nanoporous carrier material, said nanoporous carrier material having a first color in said first mode and a second color in said second mode upon ligation of an analyte, preferably wherein said metal ion having a halide counter ion such as chloride. The nanoporous silica material is synthesized using the fumed silica Cab-O-Sil. The metal ion may be iron for binding of carboxylic acids from bacteria and/or alkyl amines from lipid oxidation for detection of food status and/or for detection of bacteria from an infected wound. The metal ion may be magnesium for detection of alcohol vapors for providing information of fruit ripening and/or for providing a physical restriction of operation of a car by detection of alcohol from the breath of a driver.

Another preferred embodiment of the invention is a digital expiry date device system comprising; a packaging material having an inner surface and an outer surface; a first transponder disposed on said inner surface and a second transponder disposed on said outer surface; a sensor portion (155) electrically connected to said first transponder for detecting food status and communicate said status to said second transponder (130), wherein said sensor portion (155) comprises a metalloporphyrin dye to configure said sensor portion for an impedance change upon binding of a gaseous analyte to said metalloporphyrin dye, wherein said second transponder (130) comprising a writeable and readable digital medium for storing data of which of said numerical segments to be configured in said first mode (112*a*) and said second mode (112*b*), wherein said second transponder is arranged on said substrate (101) electrically coupled to said integrated display driver circuitry (120), wherein said plurality of digit segments are configured for said writable and readable digital medium with said transponder (130); a printed numerical array (102) comprising a plurality of said digit segments (112*a*, 112*b*) disposed on said substrate (101) for providing a variable expiration, wherein said plurality of digit segments (112*a*, 112*b*) have a respective first illuminated or colored mode and a second colorless mode;

an integrated display driving circuit (120) disposed on said substrate electrically connected to said plurality of digit segments for logical switching to said first or said second mode, wherein said plurality of digit segments are configured for the expiry of a perishable product, and wherein said second transponder (130) measuring an impedance greater than a threshold for edible food said at least one digit is displayed that includes 2-7 of said plurality of digit segment of said first mode, preferably wherein said substrate (101) comprises an adhesive surface for attachment on the outside of a package. The integrated display driver circuitry (220) may be configured to provide a digital counter (205) for counting down the remaining days of consumption for a food product.

The foregoing embodiments and advantages are merely exemplary and are not to be construed as limiting the present disclosure. The present teachings of the sensing ink can be readily applied to other kinds of machine-to-machine communication or Internet of Things systems. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims. Even if modifications and changes can be proposed by the skilled person it is the intention of the inventor that the scope of the invention comprises all changes and modifications that reasonably falls within the scope for the contribution to the state of the art. The features of different embodiments can be combined with other embodiments described herein mutatis mutandis. The scope of the invention is only limited by the appended claims.

The invention claimed is:

1. A digital expiry date device system comprising;
a packaging material having an inner surface and an outer surface;
a first transponder disposed on said inner surface and a second transponder disposed on said outer surface;
a sensor portion electrically connected to said first transponder for detecting food status and communicate said status to said second transponder,
wherein said sensor portion configured to an impedance change upon binding of a gaseous analyte to said sensor portion to a metalloporphyrin dye on said sensor portion,
wherein said second transponder comprising a writeable and readable electrochromic display with a set of number segments;
wherein said set of number segments are configured in a first mode and a second mode;
wherein said set of number segments include 2-7 segments with said first mode and said second mode to configure to readable digits,
wherein said set of number segments are configured for the expiry of a perishable product, and wherein said first transponder measuring an impedance greater than a threshold for edible food said at least one number segment is displayed that includes 2-7 segment of said first mode to readable digits,
wherein said first mode is illuminated or colored,
wherein said second mode is colorless.

2. The digital expiry date device system according to claim 1, wherein said electrochromic display is configured to provide a digital counter for counting down the remaining days of consumption for a food product.

3. The digital expiry date device system according to claim 1, wherein said sensor portion comprising;
said metalloporphyrin dye having the Formula I;

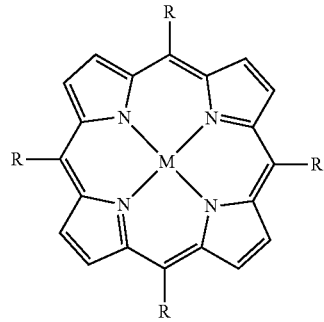

Formula I wherein M is a metal ion and R is alkyl or aryl;
a nanoporous carrier material comprising a plurality of particles with a size less than 5 μm, said plurality of particles having a plurality of pores with a pore size in the range 5-50 nm, wherein said metalloporphyrin dye is bound to said nanoporous carrier material.

4. The digital expiry date device system according to claim 3, wherein said nanoporous silica material is synthesized using a fumed carrier Cab-O-Sil.

5. The digital expiry date device system according to claim 3, wherein said nanoporous carrier material is a silica with MCM-41 structure and having a pore size of 3.5 nm.

6. The digital expiry date device system according to claim 3, wherein said metal ion is iron for binding of carboxylic acids from bacteria and/or alkyl amines from lipid oxidation for detection of food status and/or for detection of bacteria from an infected wound.

7. The digital expiry date device system according to claim 3, wherein said metal ion is magnesium for detection of alcohol vapors for providing information of fruit ripening and/or for providing a physical restriction of operation of a car by detection of alcohol from the breath of a driver.

8. The digital expiry date device system according to claim 3, wherein said metal ion having a halide counter ion such as chloride.

* * * * *